(12) United States Patent
Perez et al.

(10) Patent No.: US 7,527,645 B2
(45) Date of Patent: May 5, 2009

(54) DELIVERY SYSTEM FOR ENDOLUMINAL IMPLANT

(76) Inventors: Juan I. Perez, 678 Bellflower Ave. #22, Sunnyvale, CA (US) 94086; Shuji Uemura, 707 Leahy St., Apt. 233C, San Mateo, CA (US) 94404; Arnold M. Escano, 2095 Denise Dr., Santa Clara, CA (US) 95050; Mark Lemere, 856 Castro St., San Francisco, CA (US) 94114; Richard Newhauser, 3857—18th St., San Francisco, CA (US) 94114

( * ) Notice: Subject to any disclaimer, the term of this patent is extended or adjusted under 35 U.S.C. 154(b) by 86 days.

(21) Appl. No.: 11/262,145

(22) Filed: Oct. 28, 2005

(65) Prior Publication Data

US 2006/0036314 A1 Feb. 16, 2006

Related U.S. Application Data

(63) Continuation of application No. 10/400,769, filed on Mar. 27, 2003, now Pat. No. 6,984,244.

(51) Int. Cl.
*A61F 2/06* (2006.01)
(52) U.S. Cl. .................... 623/1.23; 623/1.12; 623/1.14; 623/1.36
(58) Field of Classification Search ....... 623/1.11–1.14, 623/1.23, 1.36; 606/191, 192, 194
See application file for complete search history.

(56) References Cited

U.S. PATENT DOCUMENTS

| | | | |
|---|---|---|---|
| 4,848,343 A | 7/1989 | Wallsten et al. | |
| 5,160,325 A | 11/1992 | Nichols et al. | |
| 5,190,520 A | 3/1993 | Fenton, Jr. et al. | |
| 5,344,402 A | 9/1994 | Crocker | |
| 5,360,401 A | 11/1994 | Turnland et al. | |
| 5,609,627 A | 3/1997 | Goicoechea et al. | |
| 5,700,269 A | 12/1997 | Pinchuk et al. | |
| 5,911,739 A * | 6/1999 | Kordis et al. ................. | 607/122 |
| 6,029,671 A | 2/2000 | Stevens et al. | |
| 6,165,213 A | 12/2000 | Goicoechea et al. | |
| 6,302,906 B1 | 10/2001 | Goicoechea et al. | |
| 6,391,051 B2 | 5/2002 | Sullivan, III et al. | |
| 6,413,269 B1 * | 7/2002 | Bui et al. .................... | 623/1.11 |
| 6,843,802 B1 * | 1/2005 | Villalobos et al. .......... | 623/1.12 |

* cited by examiner

*Primary Examiner*—William H. Matthews
(74) *Attorney, Agent, or Firm*—RatnerPrestia

(57) ABSTRACT

Delivery systems and methods for delivering modular endovascular graft devices that allow one portion of the repair device to be deployed while maintaining control of the other portions. One system includes an elongate inner member including an anchor stop ring, the anchor stop ring including a plurality of recesses, each sized to receive a portion of the trunk portion and embedding portion of a respective hook in the delivery configuration, each embedding portion extending radially outwardly at an acute angle relative to the trunk portion in the delivery configuration. The delivery systems are simpler to use, easier to manufacture and facilitate better packing of the repair device.

10 Claims, 12 Drawing Sheets

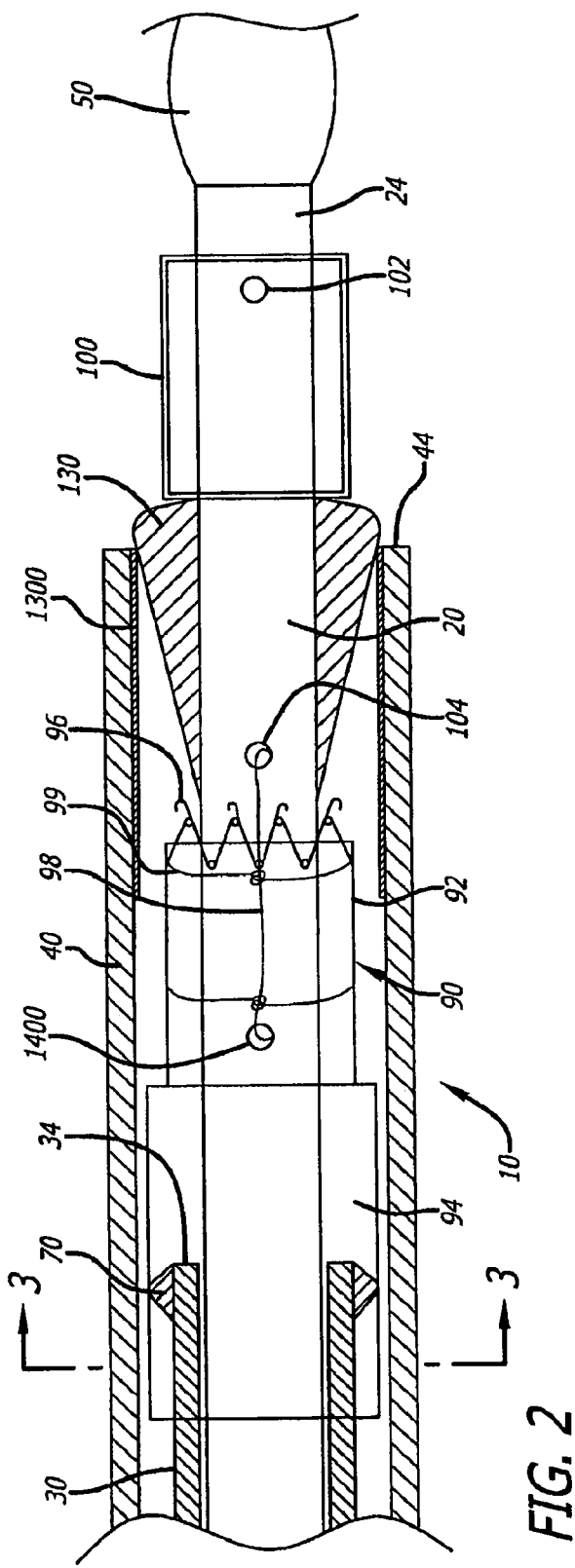
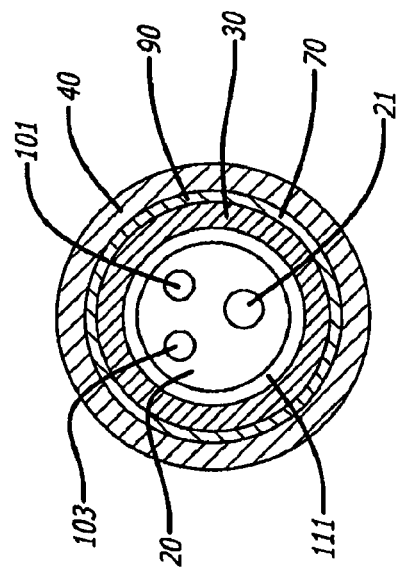
FIG. 2
FIG. 3

DELIVERY SYSTEM FOR ENDOLUMINAL IMPLANT

This application is a continuation of application Ser. No. 10/400,769, filed Mar. 27, 2003 now U.S. Pat. No. 6,984,244.

BACKGROUND OF THE INVENTION

This invention relates to systems and methods for delivering and deploying endovascular graft components within the vasculature of a patient.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape-with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods of delivering and deploying these grafts. The drawbacks of current methods of delivery and deployment of endovascular graft components include delivery systems that are complicated to use and expensive to manufacture and difficulty in assembling the individual components in-situ.

Many delivery systems have three or more catheters coaxially disposed in order to provide adequate control over the endovascular graft and to facilitate inflating an expandable balloon as well as manipulating a release mechanism for deploying the graft. Such systems may be difficult for a single physician to use and, therefore, require additional personnel. The complexity of such delivery systems adds to the difficulty of use as well as the cost of production.

A lack of adequate healthy tissue near the aneurysm being treated provides difficulty with adequately anchoring the main body portion of a modular endovascular graft. If the aneurysm extends too close to the bifurcation of the vasculature, there may be a lack of healthy tissue to adequately anchor the limb support branches of the main body component. One method known in the art is to allow the limb support portions of the main body component to float freely in the aneurysm until limb components are delivered and deployed. However, this method presents difficulties with deploying the limb components of the modular endovascular graft within a main body component having limb support portions that are not anchored.

In a situation where an endovascular graft configured with superior and inferior anchoring devices is being employed to repair vasculature, it is often desirable to be able to deploy the superior anchoring device prior to deploying the inferior anchoring device. It is also often desirable to minimize the interference between the inferior anchoring device and other components of a delivery system. Although there has been some success in this area, there is nevertheless a need for a mechanism which effectively and consistently accomplishes these goals.

With regard to the method of delivery and deployment of endovascular graft components, there therefore exists a need for a endovascular graft delivery system that limits the number of components which must be manipulated, can be easily operated by a single technician without decreased reliability or additional risk to the patient, and facilitates control of graft deployment as well as control of a previously deployed main body component in order to deliver and deploy limb components therein. The devices and methods of the present invention addresses these and other needs.

SUMMARY OF THE INVENTION

Briefly and in general terms, the present invention is embodied in delivery systems and methods for delivering and deploying a medical repair device in vasculature. The delivery systems and methods minimize redundancy and are relatively easy to operate or perform as well as allowing increased control over a partially deployed component.

Throughout this specification, the term "proximal" shall mean "nearest to the heart," and the term "distal" shall mean "furthest from the heart." Additionally, the term "ipsi-lateral" shall mean the limb of a bifurcated graft which is deployed using the same path through the vasculature that was used to deploy the main body component, and the term "contra-lateral" shall mean the limb of a bifurcated graft which is deployed using a second path through the vasculature which is catheterized after the main body component has been deployed. Furthermore, the term "inferior" shall mean "nearest the technician", and the term "superior" shall mean "farthest from the technician."

In one aspect of the invention, a system for delivering a medical repair device to a repair site is provided that facilitates controlled deployment of the repair device. The system consists of a sheath coaxially disposed over two elongate members and the repair device. One member is at least partially coaxially disposed over the other member such that the inner member may slide longitudinally relative to the outer member. The repair device has a proximal portion and a distal portion, each portion releasably secured to one of the members such that relative longitudinal movement between the sheath and the two members allows the repair device to be deployed one portion at a time. When used with a bifurcated graft component having a proximal portion and two distal portions, the delivery system allows the proximal portion to be deployed and secured within the vasculature and one distal portion to be deployed and accessed from the contra-lateral side while the other distal portion is held taut.

The inner member provides a guidewire lumen for the delivery system. An inflatable balloon may be provided at the superior end of the inner member with an inflation lumen facilitating inflation and deflation of the balloon via an inlet port at the inferior end. In one embodiment, the balloon is located under the repair device.

The repair device may be secured to the inner member by a release wire with a release wire lumen facilitating deployment of the repair device via an inlet port at the inferior end. In one embodiment, the inner member has a triple lumen with three inlet ports at the inferior end, the inlet ports providing guidewire access, an inflation lumen, and a release wire lumen.

The inferior end of the outer member facilitates locking the two members together, for example with a locking mechanism, thereby precluding relative movement. The superior end of the outer member facilitates releasably securing one portion of the repair device, for example with an area of raised diameter that pinches the repair device against the sheath. In one embodiment, a valve assembly with a locking mechanism is provided at the inferior end of the outer member, the locking mechanism securing the inner member to the outer member, and an inlet port in the valve assembly allows the space between the inner and outer members to be cleared by flushing with a liquid.

The repair device may have anchoring mechanisms at the proximal and distal ends and hooks to facilitate embedding the device in vasculature. The anchoring mechanisms may be self-expanding or balloon-expandable. It is contemplated that the delivery system may be used with any graft component known in the art.

In another aspect of the invention, a system for delivering a medical repair device is provided that isolates an anchoring device of the repair device from the sheath. In-one embodiment, the delivery system is configured with a hook capsule and an anchor stop ring which cooperate to both isolate an anchoring device as well as effectively enable the deployment of a proximal portion of the repair device prior to a distal portion thereof.

In yet another aspect of the invention, methods are provided for delivering the individual components of a modular medical repair device and assembling the components in-vivo. For example, the main body component of a modular endovascular graft prosthesis, having an attachment stent with hooks at the proximal end, may be delivered and deployed utilizing one delivery system of the present invention and the limb components of the modular endovascular graft prosthesis may be delivered and deployed utilizing another delivery system of the invention.

The trunk portion and the contra-lateral leg portion of the main body component are secured between the inner member and the sheath of the main body component delivery system and the ipsi-lateral leg portion is secured between the outer member and sheath. Once the delivery system is advanced to the treatment site, the sheath is retracted to deploy only the trunk portion and the contra-lateral leg portion. If a release wire is used to secure the trunk portion and/or contra-lateral leg portion of the main body component to the inner catheter, a release wire lumen in the inner member facilitates deployment.

An inflation balloon may be provided on the inner member and an inflation lumen utilized to embed the attachment hooks at the proximal end of the main body component in the vasculature. Relative longitudinal movement between the outer and inner members allows the inflatable balloon to be positioned with respect to the main body component.

Once the proximal end of the main body component is embedded in the vasculature, a limb component is delivered through the contra-lateral branch of the vessel using a limb component delivery system and attached to the contra-lateral leg portion of the main body component. The main body delivery system of the present invention facilitates holding the undeployed ipsi-lateral leg portion of the main body component taut, thereby making the contra-lateral deployment procedure easier.

Once the contra-lateral limb is attached to the main body component, the sheath of the main body component delivery system is retracted further to deploy the ipsi-lateral leg portion. An ipsi-lateral limb component is then delivered and attached to the ipsi-lateral leg portion.

Other features and advantages of the present invention will become apparent from the following detailed description taken in conjunction with the accompanying drawings, which illustrate, by way of example, the principles of the invention.

BRIEF DESCRIPTION OF THE DRAWINGS

FIG. 2 is a partial cross-sectional view of the superior end of the delivery system of FIG. 1;

FIG. 3 is a cross-sectional view across line 3-3 of FIG. 2;

DETAILED DESCRIPTION OF THE PREFERRED EMBODIMENTS

The present invention relates to systems and methods for accurately delivering and deploying medical repair devices at a treatment site within a patient's vasculature.

Figure 1:
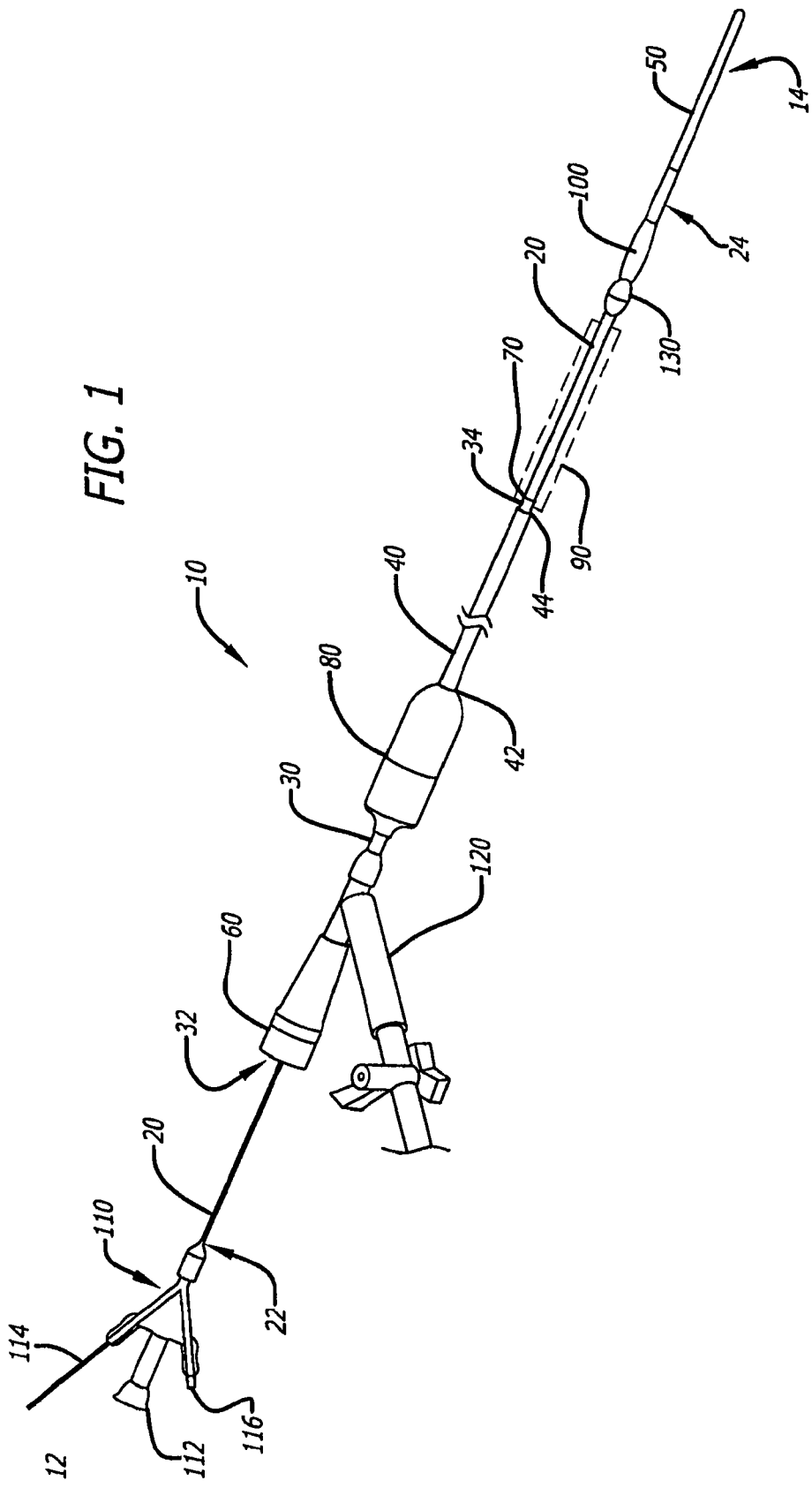
FIG. 1 is a perspective view of a delivery system of the present invention with the sheath retracted.

Referring to FIG. 1, an embodiment of a main body delivery system 10 of the present invention is shown. The delivery system 10 is defined by an inferior end 12 and a superior end 14 and has three main sections; the inner catheter 20, the main catheter 30 and sheath assembly 40.

The elongate inner catheter 20 is generally tubular and defined by an inferior end 22 and superior end 24. The inner catheter 20 extends almost the entire length of the delivery system 10 from the inferior end 12 to the superior end 14. The inner catheter 20 provides the lumen for a guidewire (not shown) over which the delivery system 10 is inserted into a body lumen.

The elongate main catheter 30 is generally tubular and defined by an inferior end 32 and superior end 34. The main catheter 30 is at least partially coaxially and slidably disposed over the inner catheter 20 such the inner catheter may slide longitudinally relative to the main catheter. A balloon lock mechanism 60 at the inferior end 32 of the main catheter 30 facilitates releasably locking the inner catheter 20 to the main catheter, thereby precluding relative movement.

The sheath assembly 40 is defined by an inferior end 42 and superior end 44 and is coaxially and slidably disposed over the portion of the inner catheter 20 and main catheter 30 to which a medical repair device 90 such as an endovascular graft component (indicated by the dotted line in FIG. 1) is releasably secured. A jacket lock mechanism 80 at the inferior end 42 of the sheath assembly 40 facilitates retracting the sheath distally, advancing the sheath proximally and releasably locking the sheath in its retracted or advanced position.

The superior end 24 of the inner catheter 20 may have an inflatable balloon 100 to facilitate expanding the repair device 90 after it has been deployed in the vasculature of a patient. A jacket guard 130 is provided at the superior end 24 of the inner catheter 20. A superior capsule 1300 is provided at the superior end 44 of the sheath assembly 40 to isolate the sheath assembly 40 from a superior anchor frame 96 at the proximal portion 92 of the repair device 90 (see FIG. 2). The jacket guard 130 is designed to receive the jacket capsule 1300 at the most proximal position of the sheath assembly 40. A nose cone 50 is attached to the distal end 24 of the inner catheter 20, the resulting smooth profile of the delivery system 10 facilitating easier maneuverability through a patient's vasculature. The jacket guard 130 and nose cone 50 may be made of radiopaque material or have radiopaque markers to facilitate positioning the main body delivery system 10 in the vasculature under fluoroscopy.

If an inflatable balloon 100 is provided, the inner catheter 20 will have an inflation lumen 101 therethrough (see FIG. 3). Furthermore, it is contemplated that the repair device 90 may be secured to the inner catheter 20 utilizing a release wire 98 (see FIG. 2) with a release wire lumen 103 provided through the inner catheter 20 (See FIG. 3). A port 110 at the inferior end 22 of the inner catheter 20 provides an exit point 112 for a guidewire (see FIG. 1) and an exit point 114 for the release wire 98 as well as access 116 for inflating and deflating the inflatable balloon 100. The port 110 has a guidewire inlet 112, inflation inlet 116, and release wire inlet 114 and also serves as a handle for retracting the inner catheter 20 distally or advancing the inner catheter proximally.

In a preferred embodiment, the inner catheter 20 consists of a Pebax nose cone 50 affixed to a hypotube, a tri-lumen coaxially affixed over the hypotube, and an SST tube covering the distal end 22. The hypotube provides the guide wire lumen and serves as the backbone of the inner catheter 20. The tri-lumen coaxially provides a hypo-tube lumen 21, the release wire lumen 103 and the inflation lumen 101 for the expandable balloon 100, which is mounted thereon (see FIGS. 2 and 3). The SST tube covers approximately the last twelve inches of the inferior end 22 of the inner catheter 20. The hypotube, tri-lumen and SST tube are fixed together by the port 110.

Figure 4:
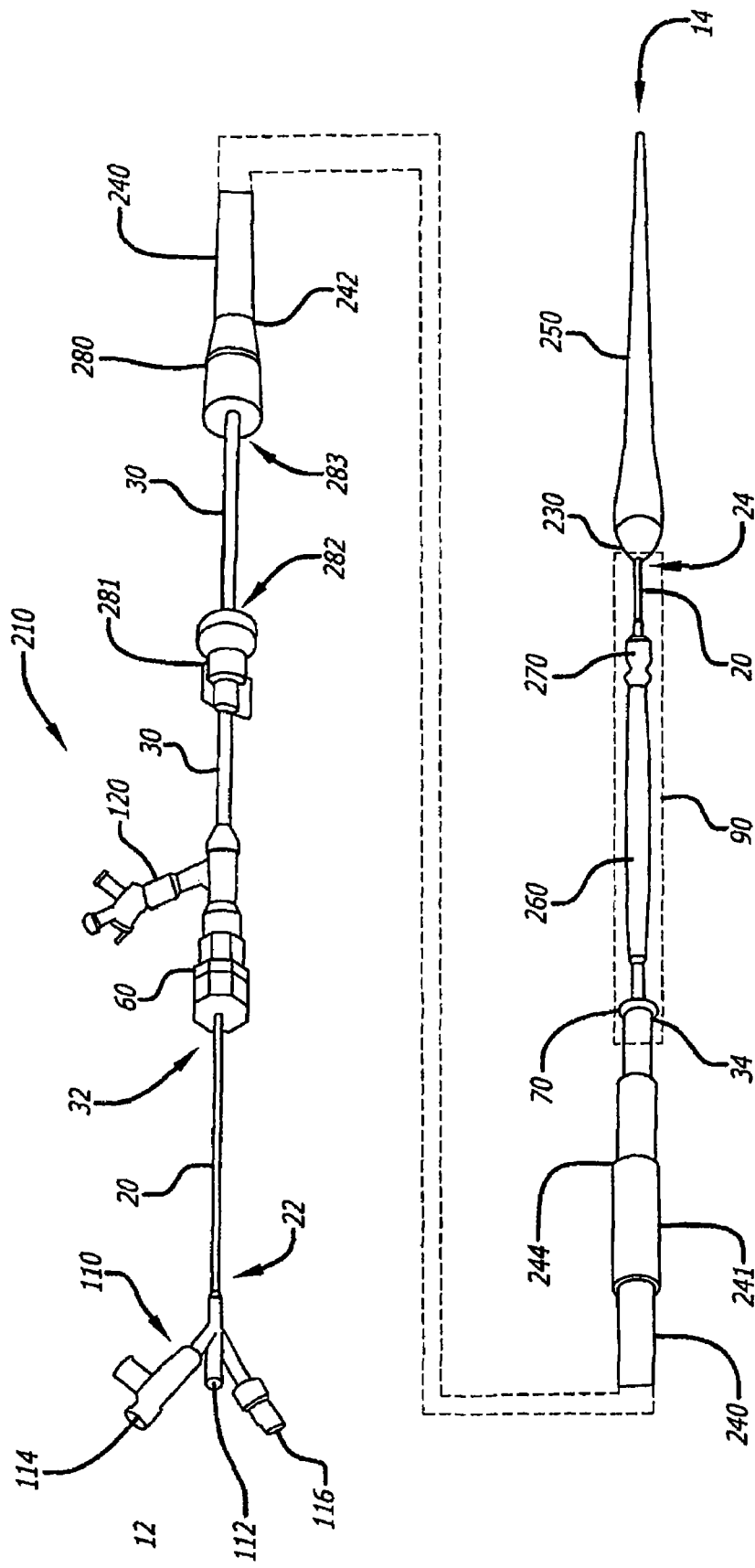
FIG. 4 is a partially fragmented perspective view of an alternate embodiment of a delivery system of the present invention with the sheath retracted.

The main catheter 30 has a localized sharp rise in diameter 70 at the superior end 34 that facilitates holding a distal end portion of a repair device 90 such as an endovascular graft component, though the structure can be employed to receive any portion of a medical device (See FIG. 4). It is contemplated that the localized sharp rise in diameter 70 may be formed as part of the main catheter 30 or may consist of, for example, a sleeve that is added after manufacture. The localized sharp rise in diameter 70 can be made of any biocompatible material that accomplishes holding a portion of a repair device 90 against the inside surface of the sheath assembly 40 and is particularly useful when the repair device is a bifurcated graft component. A valve assembly 120 at the inferior end 32 of the main catheter 30 facilitates flushing out air from the annular space 111 (see FIG. 3) between the inner catheter 20 and main catheter 30. In a preferred embodiment, the main catheter 30 consists of a Pebax shaft.

Referring to FIG. 2, one embodiment of the superior end 14 of the delivery system 10 is illustrated. The repair device 90 has a proximal portion 92 and a distal portion 94. A superior anchor frame 96 containing attachment hooks is provided at the proximal portion 92 of the repair device 90 to facilitate imbedding the repair device in a body lumen. The superior capsule 1300 isolates the attachment hooks from the sheath assembly 40, thereby preventing the hooks from interfering with retraction of the sheath assembly. A release wire 98 cooperates with a securing mechanism 99, for example suture loops held together by the release wire, to secure the proximal portion 92 and superior anchor frame 96 of the repair device 90 to the inner catheter 20. The distal portion 94 of the repair device 90 is secured between the localized sharp rise in diameter 70 at the superior end 34 of the main catheter 30 and the sheath assembly 40.

Referring to FIG. 3 with continued reference to FIGS. 1 and 2, the tri-lumen of the inner catheter 20 is illustrated. The guide wire/hypo-tube lumen 21 extends throughout the length of the inner catheter 20 and is in fluid communication with the guidewire inlet 112 in the port 110 at the inferior end 22 of the inner catheter 20. The guide wire/hypo-tube lumen 21 facilitates passing a guide wire (not shown) through the delivery system 10: The inflation lumen 101 is in fluid communication with and connects the inflation inlet 116 in the port 110 at the inferior end 22 of the inner catheter 20 to an injection orifice 102 under the inflatable balloon 100. The inflation lumen 101 facilitates inflating and deflating the inflatable balloon 100 during delivery of the endovascular graft 90. The release wire lumen 103 is in fluid communication with and connects the release wire inlet 114 in the port 110 at the inferior end 22 of the inner catheter 20 to a release wire orifice 1400 near the proximal portion 92 of the repair device 90. The proximal end of the release wire 98 is secured inside the wire orifice 104 on the capsule guard 130. The release wire lumen 103 facilitates deploying the proximal portion 92 of the repair device 90.

In operation, the delivery system 10 facilitates deploying the proximal portion 92 of the repair device 90 while maintaining control of the distal portion 94 of the repair device. When the sheath assembly 40 is retracted such that the proximal portion 92 of the repair device 90 is exposed but the superior end 44 of the sheath assembly 40 is proximal the localized sharp rise in diameter 70 at the superior end 34 of the main catheter 30, the distal portion 94 of the repair device is still held between the sheath assembly and localized sharp rise in diameter. As long as the sheath assembly 40 is not retracted further, the distal portion 94 of the repair device 90 will not deploy. The jacket lock mechanism 80 at the inferior end 42 of the sheath assembly 40 facilitates locking the sheath in its partially-retracted position.

When the release wire 98 is retracted through the release wire lumen 103 by pulling it distally from the release wire inlet 114 in the port 110, the securing mechanism 99 is released and the proximal portion 92 of the repair device 90 is deployed, the hooks of the superior anchor frame 96 embedded in the lumen wall either by self-expanding or by moving the inner catheter 20 distally and inflating the balloon 100 via the inflation lumen 101. The balloon lock mechanism 60 at the inferior end 32 of the main catheter 30 facilitates unlocking the inner catheter 20 from the main catheter so that the inner catheter and the attached balloon 100 may be moved distally until the balloon is inside the proximal portion 92 of the repair device 90.

If, for example, the repair device 90 is the main body component of a modular bifurcated prosthesis, the trunk portion and contra-lateral limb portion may be releasably secured to the inner catheter 20 by the release wire 98 and the ipsi-lateral limb portion may be held between the localized sharp rise in diameter 70 at the superior end 34 of the outer catheter 30 and the sheath assembly 40. The delivery system 10 facilitates deploying the trunk portion and contra-lateral limb portion of the main body component 90 while maintaining control of the ipsi-lateral limb portion. In this manner, accessing and deploying a limb component inside the contra-lateral limb portion of the main body component 90 is simplified since the physician may hold the ipsi-lateral limb portion taut while the contra-lateral side is accessed. It is contemplated that the delivery system 10 of the present invention may be utilized whenever it is desired to deploy one portion of a repair device 90 while maintaining control over the other portions.

Referring to FIG. 4, an alternate embodiment of a main body delivery system 210 of the present invention is shown. The delivery system 210 is similar to that illustrated in FIG. 1 and further includes a stopper 281, an aortic frame stop ring 270 and a superior capsule 241, and the inflatable balloon 260 is located underneath the repair device 90.

The stopper 281, which can be manipulated to releasably attach to the main catheter 30, provides a safeguard against retracting the sheath assembly 240 too far during the various stages of deploying a repair device 90, for example the main body component of a modular bifurcated prosthesis (see FIGS. 8-11). When the stopper 281 is attached to the main catheter 30, the sheath assembly 240 cannot be retracted past the stopper 281 even if the jacket lock mechanism 280 is unlocked. It is contemplated that the superior end 282 of the stopper 281 and inferior end 283 of the jacket lock mechanism 280 may contain a mechanism (not shown) for releasably attaching the jacket lock mechanism to the stopper, thereby allowing them to be retracted as a single unit. With the stopper 281 inhibiting retraction of the sheath assembly 240, the physician can more efficiently manipulate the delivery system 210 since he does not have to monitor the longitudinal position of the jacket lock mechanism 280 with respect to the main catheter 30, thereby allowing him to concentrate on the deployment process under fluoroscopy.

In operation, the stopper 281 may be tightened at a location along the main catheter 30 such that when the sheath assembly 240 is retracted until it contacts the stopper 281, the proximal portion 92 of the repair device 90 is exposed but the superior end 244 of the sheath assembly 240 is proximal the localized sharp rise in diameter 70 at the superior end 34 of the main catheter 30, thereby holding the distal portion 94 of the repair device between the sheath assembly and localized sharp rise in diameter. When it is desired to deploy the distal portion 94 of the repair device 90, the stopper 281 is released from the main catheter 30, thereby allowing the stopper 281 and jacket lock mechanism 280 to be retracted such that the superior end 244 of the sheath assembly 240 is distal the localized sharp rise in diameter 70 at the superior end 34 of the main catheter.

The aortic frame stop ring 270 is attached near the superior end 24 of the inner catheter 20 just proximal the inflatable balloon 260. A jacket guard 230 is located at the superior end of the inner catheter 20 just distal the nose cone 250. Both may be made of radiopaque material. The aortic frame stop ring 270 isolates the superior anchor frame 96 from the rest of the proximal portion 92 of a repair device 90 (see FIG. 6) and may provide a marker by which the distal end of the superior anchor frame can be located during operation under fluoroscopy, thereby facilitating precise deployment. A superior capsule 241 attached to the superior end 244 of the sheath assembly 240 covers the superior anchor frame 96 when the sheath assembly is advanced proximally, thereby preventing the hooks of the superior anchor frame from tearing the sheath assembly.

Figure 5:
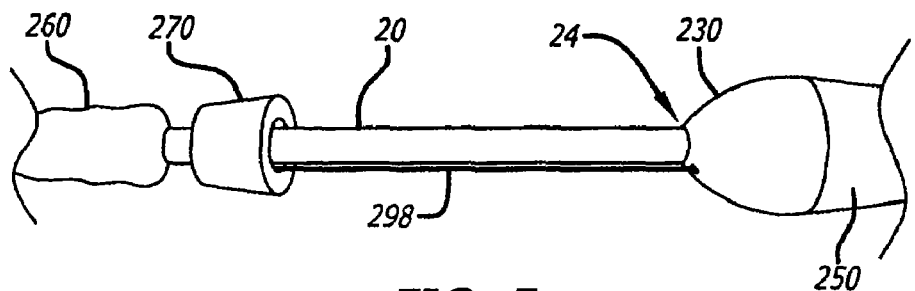
FIG. 5 is a partial perspective view of the superior end of the delivery system of FIG. 4 without the repair device.
Figure 6:
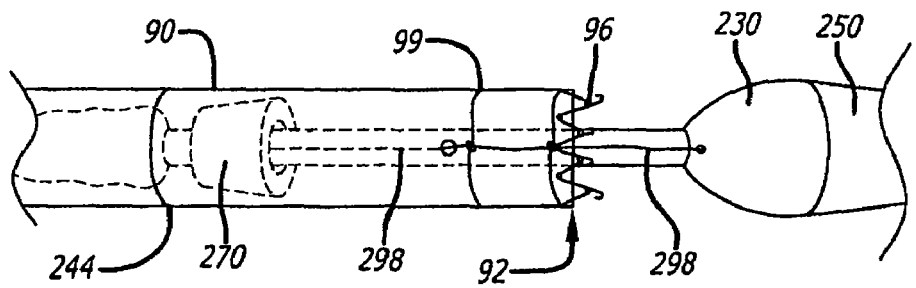
FIG. 6 is a partial perspective view of the superior end of the delivery system of FIG. 4 showing the proximal portion of the repair device.

As illustrated in FIGS. 5 and 6, the bare hypotube of the inner catheter 20 between the aortic frame stop ring 270 and jacket guard 230 provides a space for the superior anchor frame 96 of the repair device 90. The release wire 298 is routed through the release wire lumen 103 and terminates in the jacket guard 230.

In operation, the sheath assembly 240 is retracted such that the superior capsule 241 is distal the superior anchor frame 96. The proximal portion 92 of the repair device 90 and superior anchor frame 96 may then be deployed by pulling the release wire 298 distally from the release wire inlet 114 in port 110.

Figure 7:
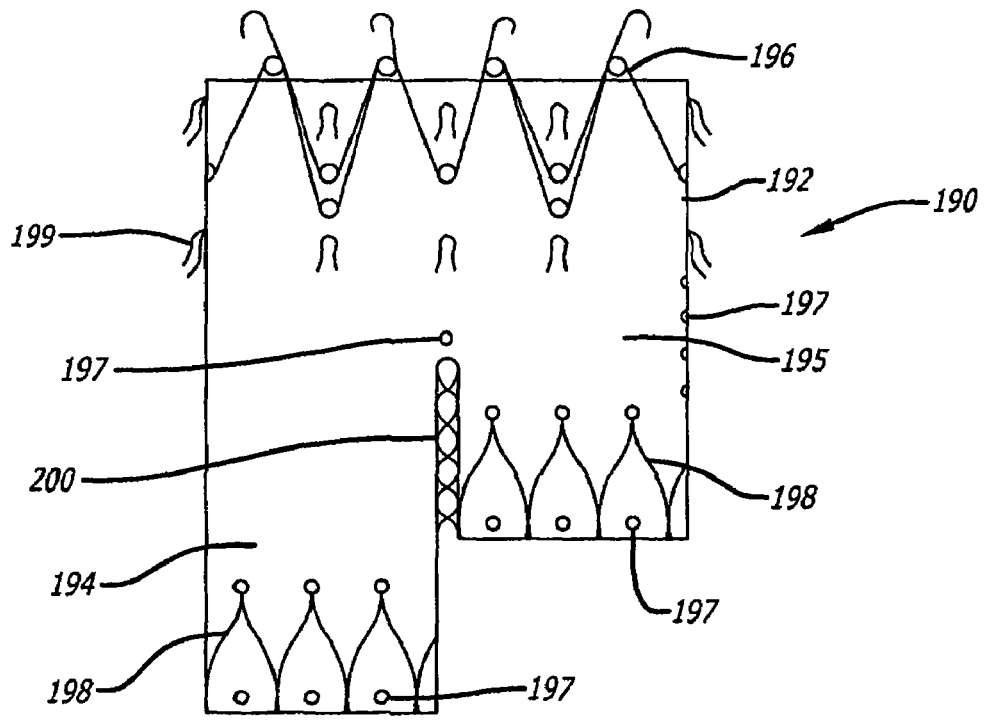
FIG. 7 is a schematic view of a main body component of a modular bifurcated graft prosthesis of the type that may be delivered using the delivery system of FIG. 4.

Referring to FIG. 7, a typical main body component 190 of a modular bifurcated endovascular graft prosthesis of the type used in the system of FIG. 4 is shown. The main body component 190 includes a trunk portion 192 and two limb portions 194, 195. The main body component 190 is preferably made of a woven Polyethylene Terephthalate (PET) material.

An aortic attachment system 196, having hooks for imbedding in the vasculature of a patient, is provided at the proximal end of the trunk portion 192. Radiopaque markers 197 along the trunk 192 portion, at the crotch and at the distal end of the limb portions 194, 195 facilitate visualization under fluoroscopy. Self-expanding port stents 198, preferably made of Nitinol, at the distal end of the limb portions 194, 195 provide patency for cannulation and consistent interface when attaching a limb component (see FIG. 16) to the main body component 190. Fuzzy tufts of yarn 199 on the trunk portion 192 just distal the aortic attachment system 196 facilitate better attachment in the vasculature of a patient. The limb portions 194, 195 may be secured to each other by sutures 200 or other means to facilitate better control during deployment of the limb portions during in situ assembly.

Note that the main body component 190 has no stent structure or support between the aortic attachment system 196 and port stents 198 at the distal end of the limb portions 194, 195. This area, consisting only of graft material, facilitates placing the inflatable balloon 260 under the main body component 190 while still maintaining a small delivery profile.

The inflatable balloon 260 is preferably made of a PET material although other materials such as polyurethane are contemplated. It is contemplated that a balloon 260 with an inflation diameter of 24 mm, 26 mm or 28 mm may be packed to a profile of 0.166" and a balloon with an inflation diameter of 30 mm or 32 mm may be packed to a profile of 0.186". With the balloon 260 located under the repair device 90, the delivery system 210 is easier to use since the packed inflatable balloon adds no additional diameter to the delivery system 210 distal the superior anchor frame 96. The balloon 260 can be made of Pellethane 2363-65D which is a thermoplastic polyurethane elastomer made up of diisocyanate and diol hard segment and polyether soft segment with durometer hardness of 62, flexural modulus of 32,000 psi, tear strength of 1100 Pli and elongation at break elasticity of 450%. The balloon operates 0.5 to 5 atmospheres in a balloon outer diameter range from 12 to 32 mm. This material has unique properties including semi-compliant and compliant distension attributes, excellent flexibility, low profile, good refold and fast inflation and deflation times.

Referring to FIGS. 8-11, a method of utilizing the main body delivery system 210 of the present invention to deploy the main body component 190 illustrated in FIG. 7 and assemble a modular bifurcated prosthesis in situ is illustrated. The repair device 190 is the main body component of the modular bifurcated prosthesis. The main body component 190 is packed in the delivery system 210 with the inner catheter 20 inside the trunk portion 192 and ipsi-lateral limb portion 194 while the contra-lateral limb portion 195 is folded back and over the ipsi-lateral limb portion 194. The trunk portion 192 is releasably secured to the inner catheter 20 by a graft securing mechanism 99 in cooperation with the release wire 298. The ipsi-lateral limb portion 194 is secured between the sheath assembly 240 and localized sharp rise in diameter 70 at the superior end 34 of the outer catheter 30.

Figure 8:
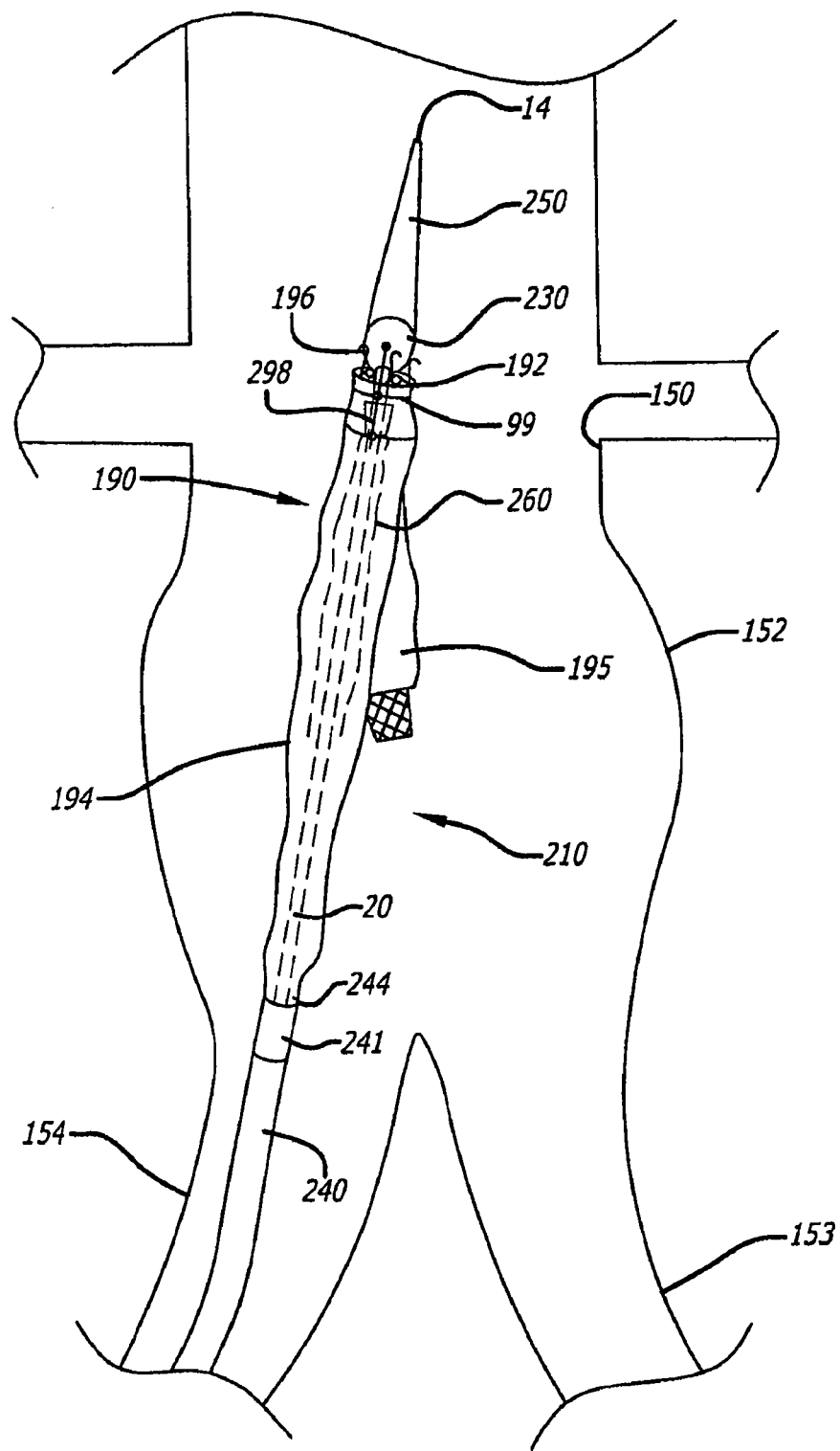
FIG. 8 is a partial cross-sectional view depicting a delivery system of the present invention inserted in the vasculature of a patient with the sheath retracted to expose the trunk portion of a bifurcated endovascular graft component.

The main body delivery system 210, having the inner catheter 20 locked to the main catheter 30 with the sheath assembly 240 advanced over the main body component 190 and locked in place, is advanced over a guide wire (not shown) through the ipsi-lateral branch 154 of the patient's vasculature 150. The main body delivery system 210 is advanced until the trunk portion 192 of the main body component 190 is located just proximal of the aneurysm 152. The sheath assembly 240 is then released via the jacket lock mechanism 280 and retracted until the superior end 244 of the jacket assembly is distal the trunk portion 192, as shown in FIG. 8. The sheath assembly 240 is then retracted further until the superior end 244 of the jacket assembly is distal the contra-lateral limb portion 194 of the main body component 190 but proximal the localized sharp rise in diameter 70 at the superior end 34 of the outer catheter 30. The sheath assembly 240 is then locked in the partially-retracted position via the jacket lock mechanism 280. In this configuration of the delivery system 210, the trunk portion 192 and contra-lateral limb portion 195 of the main body component 190 are exposed. In this configuration the trunk portion 192 of the body component 190 is still retained to the inner catheter 20 by the graft securing mechanism 99 and release wire 298.

Figure 9:
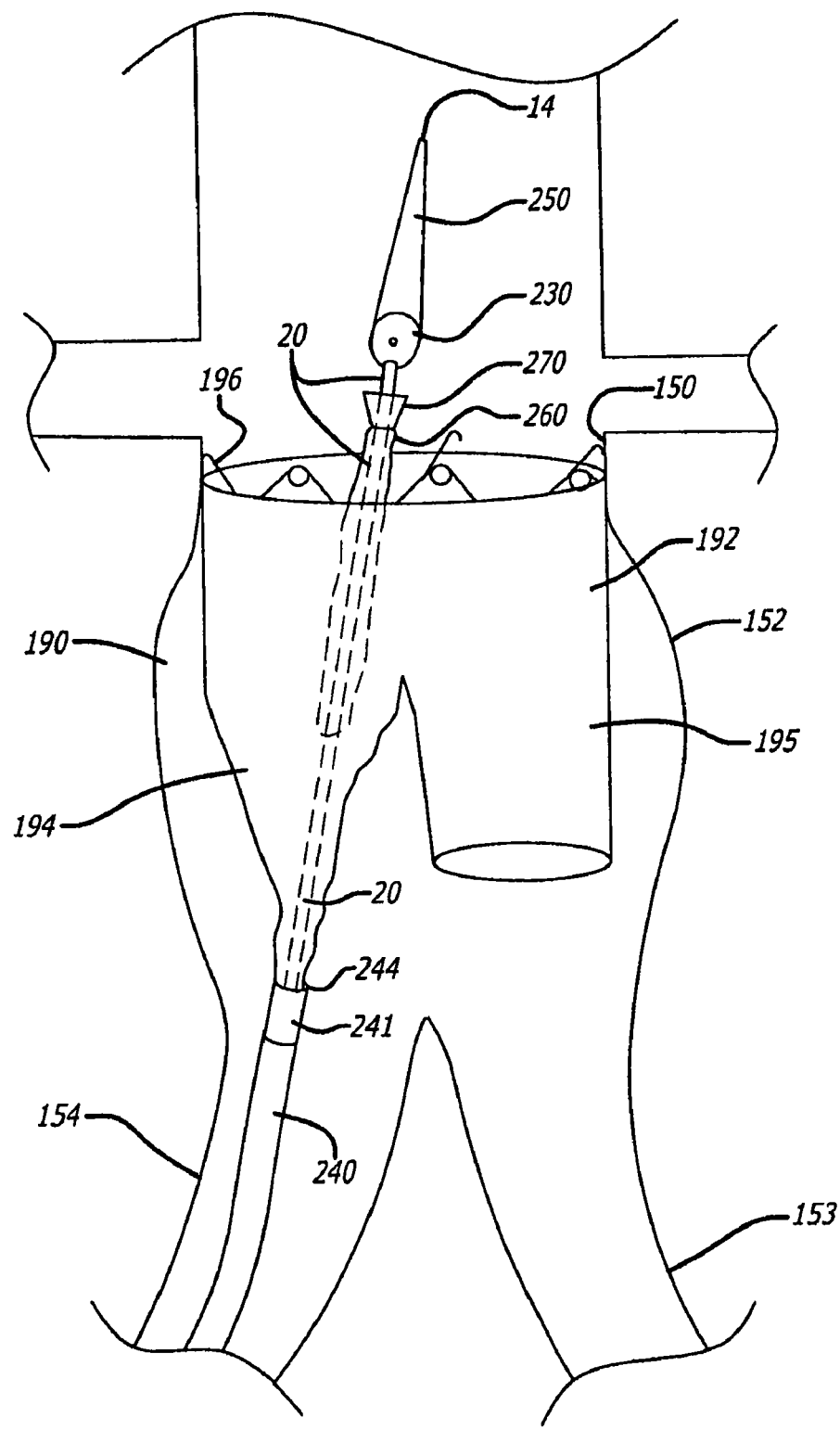
FIG. 9 is a partial cross-sectional view depicting a delivery system of the present invention inserted in the vasculature of a patient with the trunk portion and contra-lateral limb portion of a bifurcated endovascular graft component deployed and the ipsi-lateral limb portion held taut by the delivery system.

Next, as shown in FIG. 9, the release wire 298 is retracted, releasing the graft securing mechanism 99 and allowing the trunk portion 192 of the main body component 190 to deploy. The inner catheter 20 is then unlocked from the main catheter 30 via the balloon lock mechanism 60 and advanced proximally, while the main catheter 30 and sheath assembly 240 are held stationary, until the inflatable balloon 260 is located inside the anchor frame 96 of the main body component 190. The inflatable balloon 260 is inflated and deflated to embed the hooks of the aortic attachment system 196 in the lumen 150 proximal the aneurysm 152.

Figure 10:
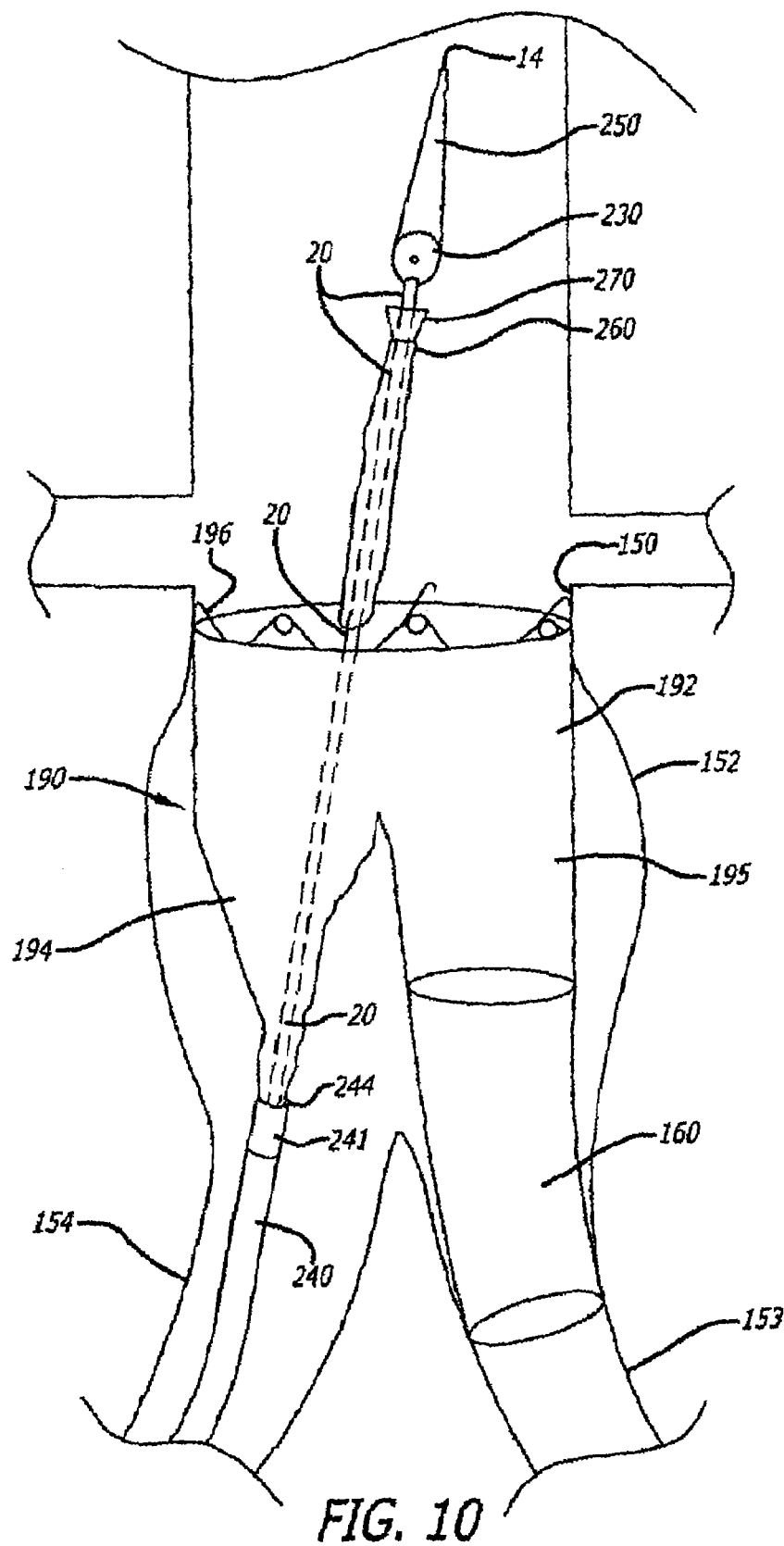
FIG. 10 is a partial cross-sectional view depicting a delivery system of the present invention inserted in the vasculature of a patient with the trunk portion and contra-lateral limb portion of a bifurcated endovascular graft component deployed and a contra-lateral limb component attached to the contra-lateral limb portion while the ipsi-lateral limb portion is held taut by the delivery system.

Next, as shown in FIG. 10, the inner catheter 20 is advanced proximally until the balloon 260 is proximal the deployed trunk portion 192 of the main body component 190 and the inner catheter 20 is then locked to the main catheter 30 via the balloon lock mechanism 60. With the delivery system 210 holding the ipsi-lateral limb portion 194, the contra-lateral branch 153 of the patient's vasculature 150 is then accessed by a method known in the art and a limb component 160 is attached to the contra-lateral limb portion 195 of the main body component 190.

Figure 11:
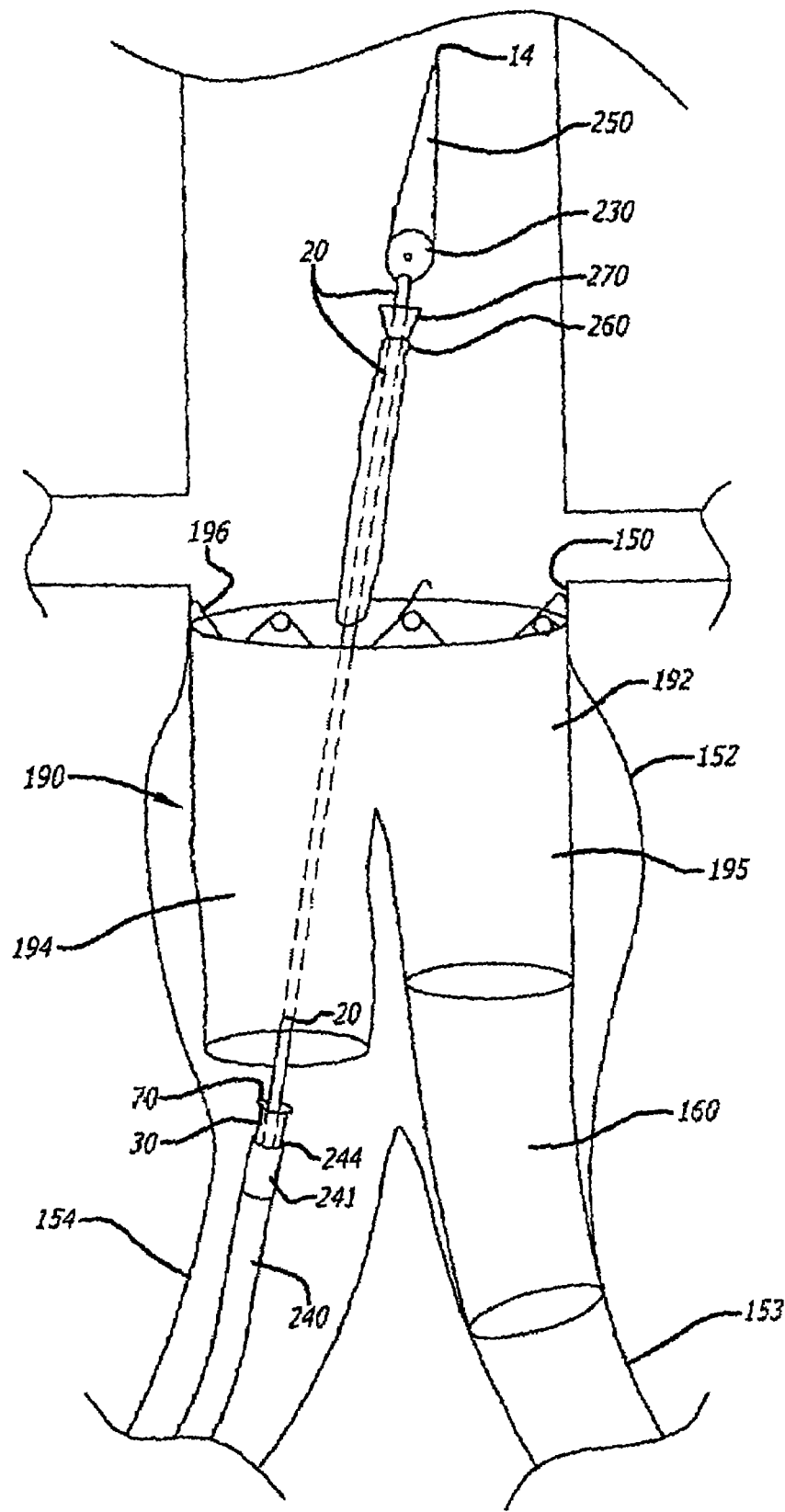
FIG. 11 is a partial cross-sectional view depicting a delivery system of the present invention inserted in the vasculature of a patient with the sheath retracted to deploy the ipsi-lateral limb portion of a bifurcated endovascular graft component.

Finally, as shown in FIG. 11, the sheath assembly 240 is released via the jacket lock mechanism 280 and retracted until the superior end 244 of the sheath assembly is distal the localized sharp rise in diameter 70 at the superior end 34 of the outer catheter 30, thereby allowing the ipsi-lateral limb portion 194 to deploy. The main body delivery system 210 may then be removed from the patient's vasculature 150 and a limb component (not shown) attached to the ipsi-lateral limb portion 194 of the main body component 190 using a method known in the art.

Although FIGS. 8-11 illustrate the delivery of a main body component 190 of a modular bifurcated prosthesis, it is contemplated that the delivery system 210 may be utilized any time it is desired to deploy a portion of a medical repair device 90 while maintaining control of the other portions. It is also contemplated that the main body delivery system 210 may be used with a medical repair device 90 which is self-expanding without a balloon 100 provided.

The main body delivery systems, 10, 210 of the present invention are simpler to use and cheaper to build because they have less components and are easier to assemble and manufacture. Furthermore, the endovascular graft component 90 is easier to pack and it is contemplated that various graft thicknesses from 0.0045" to 0.0065" may be used.

Figure 12:
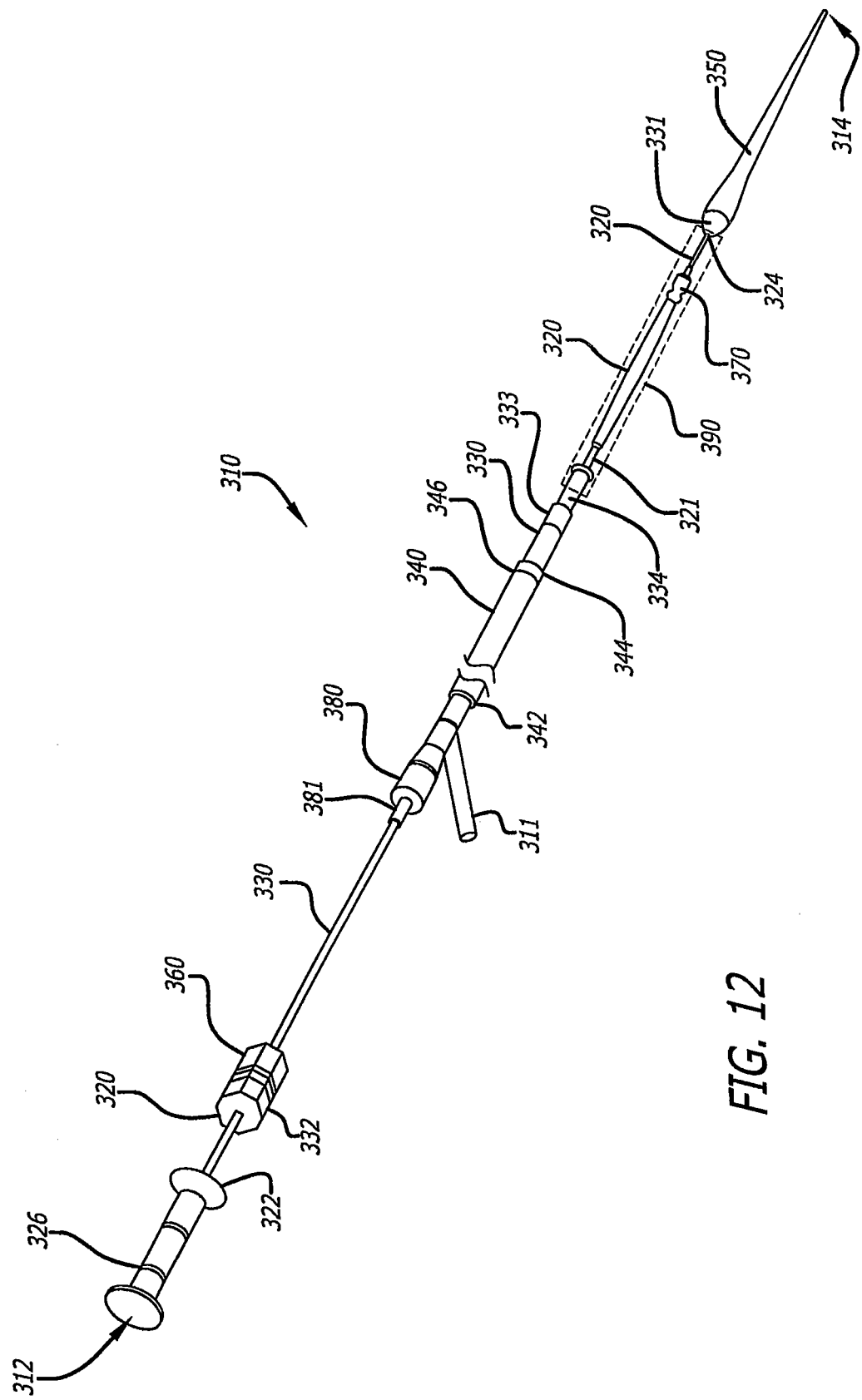
FIG. 12 is a perspective view of an alternate embodiment of a delivery system of the present invention with the sheath retracted.

Referring to FIG. 12, an embodiment of a limb delivery system 310 of the present invention is shown. The delivery system 310 is defined by an inferior end 312 and a superior end 314 and has three main sections; the inner catheter 320, the main catheter 330 and sheath assembly 340.

The elongate main catheter 330 is generally tubular and defined by an inferior end 332 and superior end 334 and is at least partially coaxially and slidably disposed over the inner catheter 320 such that the inner catheter may slide longitudinally relative to the main catheter. A distal capsule lock mechanism 360 at the inferior end 332 of the main catheter 330 facilitates releasably locking the inner catheter 320 to the main catheter, thereby precluding relative movement. The distal capsule lock mechanism 360 also serves as a handle for retracting the main catheter 330 distally or advancing the main catheter proximally.

A capsule 333 at the superior end 334 of the main catheter 330 is sized and dimensioned to receive the distal portion 394 of a medical repair device 390 such as an iliac attachment system 398 of an endovascular graft limb component (see FIG. 16), though the structure can be employed to receive any portion of a repair device. The capsule 333, which may be moved relative to the inner catheter 320, cooperates with the inner catheter to gain control of the distal portion 394 of a repair device 390. The capsule 333 can be made of any biocompatible material that accomplishes isolating the repair device 390 from the sheath assembly 340 and is particularly useful when the repair device includes hooks or barbs 410 designed to aid in implanting the device within vasculature. The capsule 333 may be made of radiopaque material or have radiopaque markers to facilitate tracking the relative position of the capsule and inner catheter 320.

The elongate inner catheter 320 is generally tubular and defined by an inferior end 322 and superior end 324 and extends almost the entire length of the delivery system 310 from the inferior end 312 to the superior end 314. The inner catheter 320 provides the lumen for a guidewire (not shown) over which the delivery system 310 is inserted into a body lumen. A nose cone 350 is attached to the distal end 324 of the inner catheter 320, the resulting smooth profile of the delivery system 310 facilitating easier maneuverability through a patient's vasculature.

The inner catheter 320 further includes a jacket guard 331 at the superior end 324 just distal the nose cone 350, a superior stop ring 370 affixed near the superior end distal the jacket guard, an inferior stop ring 321 affixed distal the superior stop ring, and a knob 326 at the inferior end 322. The jacket guard 331, superior stop ring 370, inferior stop ring 321 and nose cone 350 may be made of radiopaque material or have radiopaque markers to facilitate positioning the limb delivery system 310 in the vasculature of a patient.

The jacket guard 331 is similar to the jacket guard 230 illustrated in FIG. 4. The jacket guard 331 may provide a marker by which the proximal portion 392 of the repair device 390 can be located during operation under fluoroscopy. The superior stop ring 370 is similar to the aortic frame stop ring 270 illustrated in FIG. 4. The superior stop ring 370 isolates the proximal lock stent 396 from the rest of the proximal portion 392 of a repair device 390 and may provide an additional marker by which the proximal lock stent 396 of the repair device 390 can be located during operation under fluoroscopy.

The inferior stop ring 321 is attached to the inner catheter 320 such that its position is fixed relative to the nose cone 350. The stop ring 321 is sized and dimensioned to receive the distal portion 394 of a repair device 390 such as an iliac attachment system 398 of an endovascular graft limb component (see FIG. 16), though the structure can be employed to receive any portion of a medical repair device. The inferior stop ring 321 cooperates with the capsule 333 of the main catheter 330 to gain control of a distal portion 394 of a repair device 390. The inferior stop ring 321 can be made of any biocompatible material that accomplishes holding a portion of a repair device 390 in cooperation with the capsule 333 of the main catheter 330 and is particularly useful when the repair device includes hooks or barbs designed to aid in implanting the device within vasculature.

The knob 326 facilitates relative movement between the inner catheter 320 and outer catheter 330. When the distal capsule lock mechanism 360 of the main catheter 330 is unlocked, the knob 326 may be held while retracting the main catheter 330 distally, thereby exposing the inferior stop ring 321 of the inner catheter and allowing the distal portion 394 of a repair device 390 to deploy.

The sheath assembly 340 is defined by an inferior end 342 and superior end 344 and is coaxially and slidably disposed over the portion of the inner catheter 320 and main catheter 330 to which a repair device 390 is releasably secured. A jacket lock mechanism 380 at the inferior end 342 of the sheath assembly 340 facilitates retracting the sheath distally, advancing the sheath proximally and releasably locking the sheath in its retracted or advanced position. A valve assembly 311 facilitates flushing out air from the annular space between the outer catheter 330 and sheath assembly 340. The distal end 344 of the sheath assembly 340 has a radiopaque marker band 346 to facilitate positioning the repair device 390 in the vasculature of a patient utilizing fluoroscopy.

Figure 13:
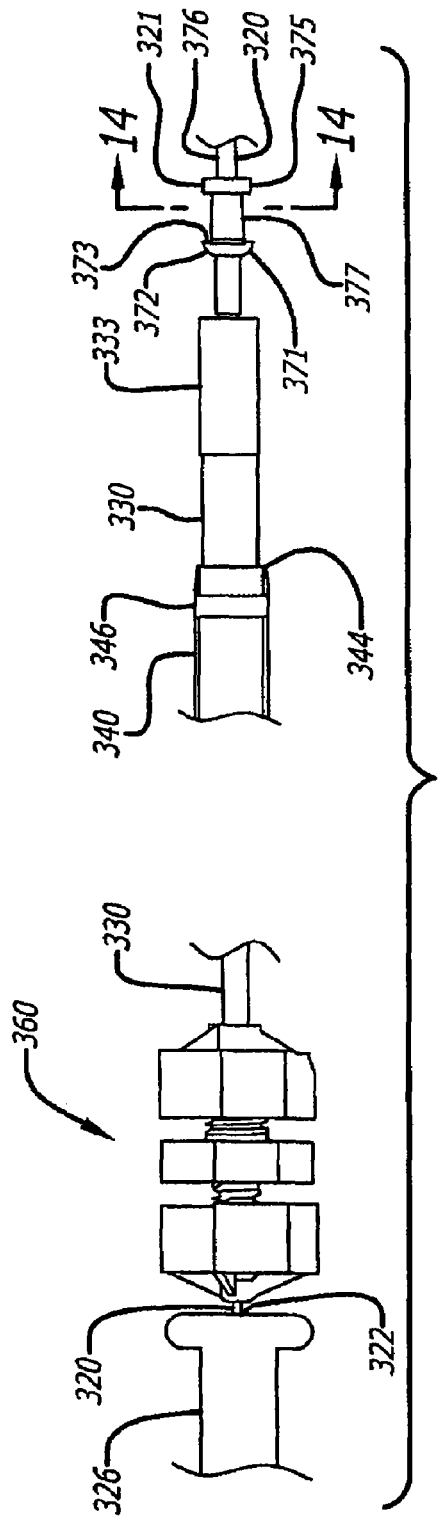
FIG. 13 is a fragmented sectional side view of the delivery system of FIG. 12 with the hook capsule retracted to expose the inferior stop ring.
Figure 14:
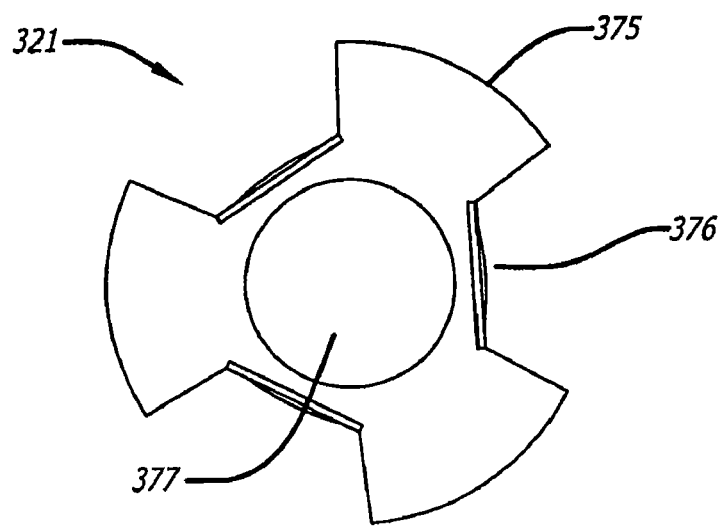
FIG. 14 is a cross-sectional view across line 14-14 in FIG. 13.

Referring to FIG. 13, one embodiment of the inferior stop ring 321 includes an inferior end portion configured with a cap 371 having a rounded inferior surface 372 and a substantially flat superior surface 373 as well as a superior end portion with a knob 375 having grooves 376 arranged to receive a radial dimension of struts of the distal portion 394 of a repair device 390, for example an iliac attachment system 398. The midsection 377 of the inferior stop ring 321 can be tapered to define a space for receiving a longitudinal dimension of an iliac attachment system 398. As can best be seen in FIG. 14, the grooves 376 are preferably located at equidistant points about the circumference of the knob 375. Although FIG. 13 depicts one embodiment of the inferior stop ring 321, it is to be understood that various other embodiments are contemplated, each of which can include specific structure for receiving and retaining the distal portion 394 of a repair device 390. The knob 375 may also have a rounder inferior surface like surface 372 of cap 371.

Figure 15:
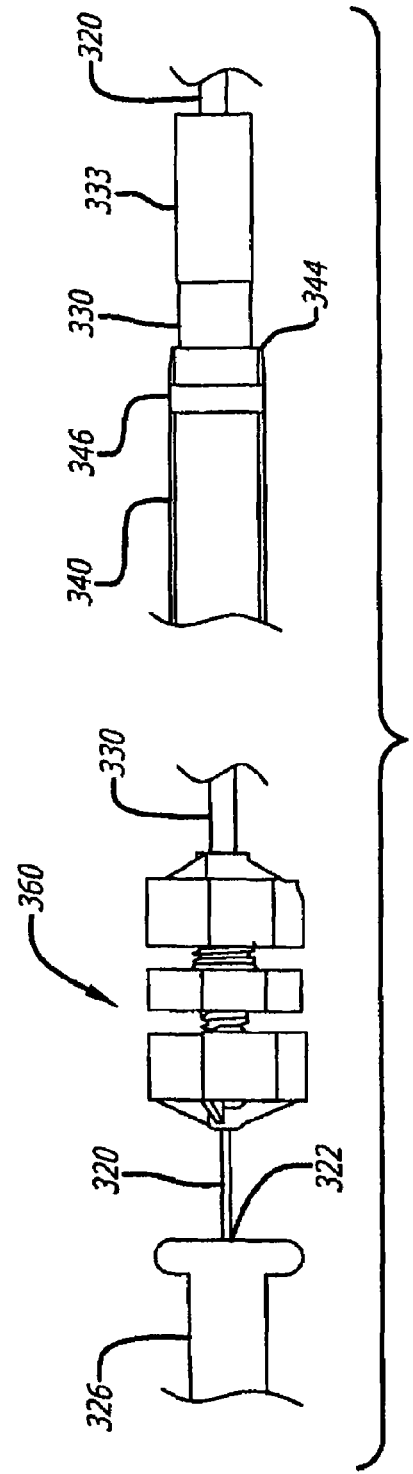
FIG. 15 is a fragmented sectional side view of the delivery system of FIG. 12 with the hook capsule covering the inferior stop ring.

As shown in FIG. 15, when the distal capsule lock mechanism 360 is advanced proximally such a gap exists between the lock mechanism and the knob 326 at the inferior end 322 of the inner catheter 320, the capsule 333 of the main catheter 330 covers the inferior stop ring 321. In operation, a distal portion 394 of a repair device 390 placed over the inferior stent stop ring 321 will be pressed against the stop ring by the capsule 333, thereby restraining it and preventing it from deploying. If the distal portion 394 of the repair device 390 is an iliac attachment system 398 of an endovascular graft limb component, the hooks will be pressed into the grooves 376 of the stop ring 321 and prevented from contacting the sheath assembly 340.

Referring again to FIG. 13, when the distal capsule lock mechanism 360 is retracted distally such that little or no gap exists between the lock mechanism and the knob 326 at the inferior end 322 of the inner catheter 320, the capsule 333 of the main catheter 330 is distal the inferior stop ring 321, no longer pressing the distal portion 394 of the repair device 390 against the stop ring. If the sheath assembly 340 has been retracted such that the superior end 344 is distal the stop ring 321, the distal portion 394 of the repair device 390 is allowed to deploy. If the distal portion 394 of the repair device 390 is an iliac attachment system 398 of an endovascular graft limb component, the hooks will be free to imbed in the vasculature of a patient or in another endovascular graft component into which the delivery system 310 has been inserted.

Figure 16:
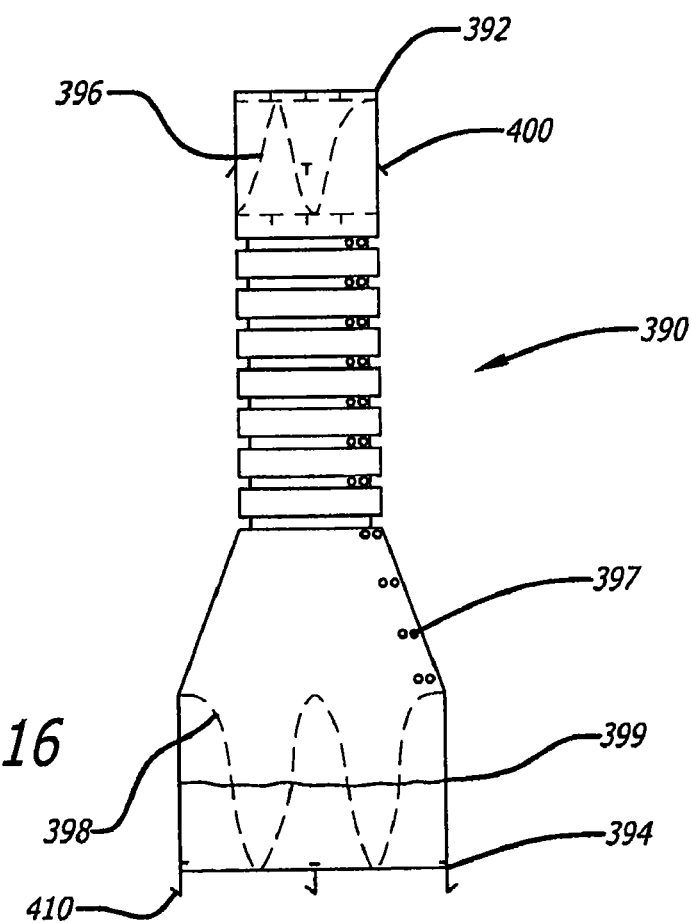
FIG. 16 is a schematic view of a limb component of a modular bifurcated graft prosthesis of the type that may be delivered using the delivery system of FIG. 12.

Referring to FIG. 16, an endovascular graft limb component 390 of the type deliverable with the delivery system 310 is shown. The limb component 390 is defined by a proximal portion 392 and a distal portion 394. The limb component preferably is made of a woven PET material.

A self-expanding lock stent 396 is provided at the proximal portion 392 of the limb component 390. The lock stent 396 has hooks 400 that protrude through the graft material for locking the limb component 390 to a limb portion 194, 195 of a main body component 190 (see FIG. 7) of an endovascular prosthesis. A self-expanding iliac attachment system 398, having hooks 410 for imbedding in the vasculature of a patient to fix the implant to the artery wall, is provided at the distal portion 394 of the limb component 390. Radiopaque markers 397 along the limb component 390 facilitate accurate deployment under fluoroscopy. Fuzzy tufts of yarn 399 near the distal portion 394 facilitate better attachment in the vasculature of a patient.

Figure 17:
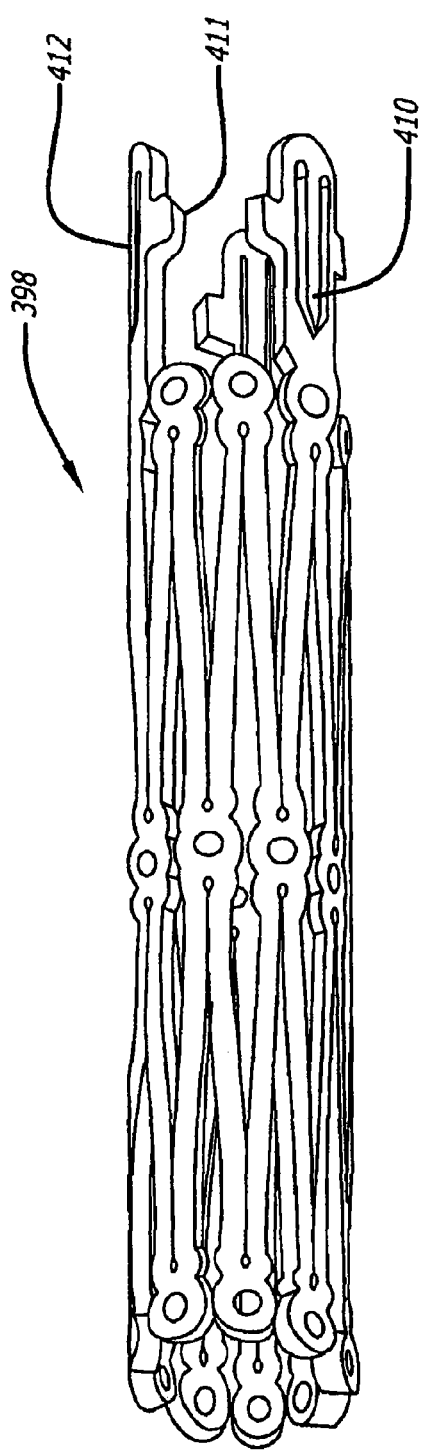
FIG. 17 is a perspective view of an iliac attachment system with "cross"-like hooks.

The hooks 410 of the iliac attachment system 398 protrude from the distal portion 394 of the limb component 390 and preferably are made of Nitinol. As shown in FIG. 17, the hooks 410 have a profile that resembles a cross. It is contemplated that the cross may have one or more arms 411 that are essentially perpendicular to the trunk 412 of the hook 410.

Figure 18:
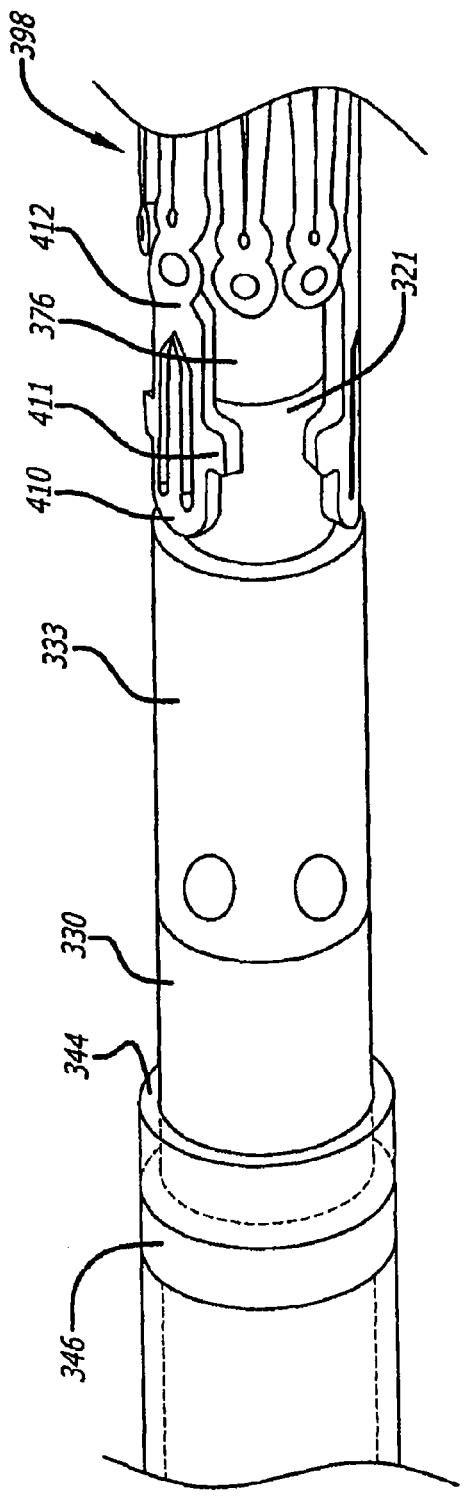
FIG. 18. is a perspective view of the superior end of the delivery system of FIG. 12 with the hook capsule retracted to expose the cross-like hooks of an iliac attachment system held in the inferior stop ring.

As shown in FIG. 18, when the limb component 390 is mounted in the delivery system 310, the trunk 412 of the hook 410 sits in a groove 376 of the inferior stop ring 321 and the arms 411 of the hook rest distal to the groove. When the capsule 333 of the main catheter 330 covers the inferior stop ring 321, the arms 411 of each hook 410 are effectively captured between the capsule and the stop ring.

It will be apparent that, when the distal capsule lock mechanism 360 is retracted to remove the capsule 333 of the main catheter 330 from the inferior stop ring 321 before the sheath assembly 340 is retracted, the hooks 410 of the iliac attachment system 398 would prevent the sheath assembly from being retracted. The movement of the inner catheter 320 relative to the main catheter 330 may, therefore, be limited by the design as a safety precaution. Such a precaution can be making the spacing between the distal capsule lock mechanism 360 and knob 326 shorter than the spacing between the proximal end 344 of the sheath assembly 340 and the hooks 400 of the limb component. This design limitation ensures that in the event of reverse-order deployment or misuse, the hooks 400, 410 of the lock stent 396 and the iliac attachment system 398, respectively, will remain inside the delivery system 310, thereby allowing the delivery system to be removed from the patient without further damage to the vasculature.

In use, the delivery system 310 is loaded with a repair device 390, such as the endovascular graft limb component shown in FIG. 16. The repair device 390 is loaded such that the lock stent 396 rests in the space between the superior stop ring 370 and jacket guard 331 and the hooks 410 of the iliac attachment system 398 rest against the inferior stop ring 321 as shown in FIG. 18. The main catheter 330 is advanced proximally as shown in FIG. 15 and locked to the inner catheter 320 using the distal capsule lock mechanism 360 such that the capsule 333 of the main catheter covers the inferior stop ring 321, thereby pressing the hooks 410 of the iliac attachment system 398 against the inferior stop ring. The sheath assembly 340 is advanced and locked using the jacket lock mechanism 380 such that the sheath assembly covers the repair device 390, its superior end 344 forming a smooth transition with the nosecone 350.

The delivery system 310 is advanced through vasculature to a repair site. The jacket lock mechanism 380 is unlocked and the sheath assembly 340 is retracted to allow deployment of the lock stent 396 of the repair device 390 while the hooks 410 of the iliac attachment system 398 of the repair device are held between the inferior stop ring 321 and capsule 333. When the sheath assembly 340 is retracted such that the superior end 344 is distal the superior end 334 of the main catheter 330, the iliac attachment system 398 of the repair device 390 will deploy with the exception of the hooks 410 which are still pressed against the inferior stop ring 321 by the capsule 333.

When it is time to deploy the hooks 410 of iliac attachment system 398 of the repair device 390, the distal capsule lock mechanism 360 is unlocked and the main catheter 330 is retracted distally while holding the knob 326. Such manipulation causes the capsule 333 to slide distally from the inferior stop ring 321 as shown in FIG. 13, thereby releasing the hooks 410 of the iliac attachment system 398 and permitting the completed implantation of the repair device 390 at the repair site.

Although use of the delivery system 310 was described with reference to the limb component 390 shown in FIG. 16, it is contemplated that the delivery system 310 may be utilized in the deployment of any multi-component repair device. The delivery system 310 facilitates reliable, simple and safe deployment of a repair device having opposing hooks at both ends through a small and tortuous path. It is further contemplated that the delivery system 310 may be scaled up or down to isolate and deploy hooks, barbs or eyelets of any size.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A system for repairing vasculature, comprising:
a medical repair device including at least one anchor having a plurality of hooks, each hook including a trunk portion and an embedding portion, each embedding portion moves between a delivery configuration and a deployed configuration;
an elongate inner member including an anchor stop ring, the anchor stop ring including a plurality of recesses, each recess receiving a portion of the trunk portion and embedding portion of a respective hook in the delivery configuration, each embedding portion extending radially outwardly at an acute angle relative to the trunk portion in the delivery configuration; and
an elongate outer member including a capsule, the elongate outer member slidably receiving the elongate inner member and the capsule receiving the anchor stop ring.

2. The system of claim 1, wherein:
the outer member further comprises a mechanism to releasably secure the outer member to the inner member;
a sheath slidably disposed over the outer member, inner member and repair device; and
the sheath further comprises a mechanism to releasably secure the sheath to the outer member.

3. The system of claim 1, wherein the trunk portion has a profile with an enlarged cross-section at the distal end.

4. The system of claim 1, wherein the anchor is retained between the anchor stop ring and the capsule.

5. A system for repairing vasculature, comprising:
a medical repair device including at least one anchor having at least one hook having a trunk portion and an embedding portion;

an elongate inner member including an anchor stop ring, the anchor stop ring including a plurality of recesses receiving a portion of the trunk and embedding portions of the at least one hook of the anchor; and an elongate outer member including a capsule, the elongate outer member slidably receiving the elongate inner member and the capsule receiving the anchor stop ring, the anchor stop ring further comprising an inferior end portion configured with a cap, the cap having a rounded inferior surface and a substantially flat superior surface.

6. The system of claim 5, the anchor stop ring further comprising a tapered midsection and wherein the recesses are defined by grooves formed in a superior end portion of the anchor stop ring.

7. The system of claim 5, wherein the recesses are defined by grooves formed in an inferior part of the anchor stop ring thereby permitting the anchor stop ring to define a more rounded profile.

8. A system for repairing vasculature, comprising:

a medical repair device including at least one anchor having a plurality of hooks, each hook comprising a trunk, at least one arm extending therefrom and an embedding portion, each embedding portion having a delivery configuration and a deployed configuration;

an elongate inner member including an anchor stop ring, the anchor stop ring including a plurality of recesses sized to receive a portion of a trunk and embedding portion of a respective anchor hook in the delivery configuration, each embedding portion moving radially outwardly to an acute angle relative to each respective trunk in the deployed configuration;

an elongate outer member including a capsule, the elongate outer member slidably receiving the elongate inner member and having a mechanism to releasably secure the outer member to the inner member and the capsule receiving the anchor stop ring such that the anchor is captured between the anchor stop ring and capsule; and a sheath slidably disposed over the outer member, inner member and repair device, the sheath having a mechanism to releasably secure the sheath to the outer member.

9. A system for delivering and deploying a modular medical repair device in vasculature, comprising:

a first catheter having an elongated inner member, an elongated outer member, a first medical repair device and a sheath, the outer member coaxially disposed over a portion of the inner member such that the inner member is longitudinally slidable within the outer member, the outer member having a superior end adapted to releasably secure a distal end of the first repair device thereto, and the sheath coaxially disposed and longitudinally slidable over the inner member, outer member and first repair device such that the sheath releasably retains the distal end of the repair device against the superior end of the outer member; and a second catheter having an elongate inner member, an elongate outer member, and a second medical repair device, the inner member having an anchor stop ring with a plurality of recesses, the outer member slidably receiving the inner member and having a capsule configured to receive the anchor stop ring, the second repair device having at least one anchor with a plurality of hooks, each hook including a trunk portion and an embedding portion, each embedding portion moveable between a delivery configuration and a deployed configuration, and the anchor retained between the anchor stop ring and the capsule with a portion of each trunk portion and embedding portion retained in the recesses of the anchor stop ring in the delivery configuration, wherein each embedding portion extends radially outwardly at an acute angle relative to the trunk portion in the deployed configuration.

10. The system of claim 9, wherein the first medical repair device is a modular bifurcated endovascular main graft component and the second medical repair device is an endovascular limb component.

* * * * *